United States Patent
Andersson et al.

(10) Patent No.: US 8,722,421 B2
(45) Date of Patent: May 13, 2014

(54) MICROFLUIDIC DEVICE

(75) Inventors: Per Andersson, Uppsala (SE); Klas Allmer, Danderyd (SE); Anders Larsson, Bromma (SE)

(73) Assignee: GYROS Patent AB, Uppsala (SE)

( * ) Notice: Subject to any disclaimer, the term of this patent is extended or adjusted under 35 U.S.C. 154(b) by 285 days.

(21) Appl. No.: 11/302,713

(22) Filed: Dec. 14, 2005

(65) Prior Publication Data

US 2006/0159592 A1   Jul. 20, 2006

Related U.S. Application Data (63) Continuation of application No. 09/674,457, filed as application No. PCT/IB99/00907 on May 7, 1999, now abandoned.

(30) Foreign Application Priority Data

May 8, 1998 (GB) .................................. 9809943.5

(51) Int. Cl.
   *G01N 1/10* (2006.01)
(52) U.S. Cl.
   USPC ............ 436/180; 436/174; 422/502; 422/506
(58) Field of Classification Search
   USPC ......... 422/64, 67, 72, 99, 100, 102, 502, 503, 422/504, 506; 436/45, 174, 180
   See application file for complete search history.

(56) References Cited

U.S. PATENT DOCUMENTS

| | | |
|---|---|---|
| 3,679,367 A | 7/1972 | Negersmith |
| 4,018,652 A | 4/1977 | Lanham et al. |
| 4,077,845 A | 3/1978 | Johnson |
| 4,154,793 A | 5/1979 | Guigan |
| 4,318,994 A | 3/1982 | Meyer et al. |
| 4,381,291 A | 4/1983 | Ekins et al. |
| 4,426,451 A | 1/1984 | Columbus |
| 4,440,638 A | 4/1984 | Judy et al. |
| 4,515,889 A | 5/1985 | Klose et al. |
| 4,661,451 A | 4/1987 | Hansen |
| 4,676,274 A | 6/1987 | Brown |
| 4,676,952 A | 6/1987 | Edelmann et al. |
| 4,729,862 A | 3/1988 | Salatiello et al. |
| 4,745,072 A | 5/1988 | Ekins et al. |
| 4,756,884 A | 7/1988 | Hillman et al. |

(Continued)

FOREIGN PATENT DOCUMENTS

| | | |
|---|---|---|
| DE | 4400955 A1 | 6/1995 |
| EP | 0241140 B1 | 10/1987 |

(Continued)

OTHER PUBLICATIONS

Ahn et al., "A fully integrated micromachined magnetic particle manipulator and separator," Microelecvtronics Research Center; School of Electrical and Computer Engineering; Georgia Institute of Technology, Atlanta, GA; pp. 91-96, 1994.

(Continued)

*Primary Examiner* — Jill Warden
*Assistant Examiner* — Dwayne K Handy
(74) *Attorney, Agent, or Firm* — Fulbright & Jaworski LLP (57) ABSTRACT

A microfluidic device adapted such that the flow of fluids within the device is controlled by different surfaces of the device having different surface characteristics. Preferably the device comprises a substrate not formed from a hydrated oxide material.

22 Claims, 5 Drawing Sheets

(56) References Cited

U.S. PATENT DOCUMENTS

| | | |
|---|---|---|
| 4,762,683 A | 8/1988 | Romanauskas |
| 4,868,129 A | 9/1989 | Gibbons et al. |
| 4,917,865 A | 4/1990 | Romanauskas |
| 4,940,527 A | 7/1990 | Kazlauskas et al. |
| 4,946,795 A | 8/1990 | Gibbons et al. |
| 5,006,749 A | 4/1991 | White |
| 5,122,284 A | 6/1992 | Braynin et al. |
| 5,160,702 A | 11/1992 | Kopf-Sill et al. |
| 5,171,695 A | 12/1992 | Ekins |
| 5,173,262 A | 12/1992 | Burtis et al. |
| 5,230,866 A | 7/1993 | Shartle et al. |
| 5,242,803 A | 9/1993 | Burtis et al. |
| 5,252,294 A | 10/1993 | Kroy et al. |
| 5,304,487 A | 4/1994 | Wilding et al. |
| 5,368,704 A | 11/1994 | Madou et al. |
| 5,376,252 A | 12/1994 | Ekstrom et al. |
| 5,409,665 A | 4/1995 | Burd |
| 5,413,732 A | 5/1995 | Buhl et al. |
| 5,426,032 A | 6/1995 | Phillips et al. |
| 5,432,009 A | 7/1995 | Tabata et al. |
| 5,472,603 A | 12/1995 | Schembri |
| 5,587,128 A | 12/1996 | Wilding et al. |
| 5,593,838 A | 1/1997 | Zanzucchi et al. |
| 5,627,041 A | 5/1997 | Shartle |
| 5,635,358 A | 6/1997 | Wilding et al. |
| 5,637,469 A | 6/1997 | Wilding et al. |
| 5,650,334 A | 7/1997 | Zuk et al. |
| 5,653,939 A | 8/1997 | Hollis et al. |
| 5,660,993 A | 8/1997 | Cathey et al. |
| 5,690,841 A | 11/1997 | Elderstig |
| 5,698,162 A | 12/1997 | Belly et al. |
| 5,773,488 A | 6/1998 | Allmer et al. |
| 5,798,215 A | 8/1998 | Cathey et al. |
| 5,912,134 A | 6/1999 | Shartle |
| 5,962,081 A | 10/1999 | Ohman et al. |
| 5,992,820 A | 11/1999 | Fare et al. |
| 5,995,209 A | 11/1999 | Ohman et al. |
| 6,074,827 A | 6/2000 | Nelson et al. |
| 6,126,765 A | 10/2000 | Ohman et al. |
| 6,130,098 A | 10/2000 | Handique et al. |
| 6,143,247 A | 11/2000 | Sheppard, Jr. et al. |
| 6,143,248 A | 11/2000 | Kellogg et al. |
| 6,144,447 A | 11/2000 | Ohman et al. |
| 6,192,768 B1 | 2/2001 | Wallman |
| 6,203,291 B1 | 3/2001 | Stemme et al. |
| 6,271,040 B1 | 8/2001 | Buechler |
| 6,296,020 B1 | 10/2001 | McNeely et al. |
| 6,299,839 B1 | 10/2001 | Karunaratne et al. |
| 6,319,468 B1 | 11/2001 | Sheppard, Jr. et al. |
| 6,319,469 B1 | 11/2001 | Mian et al. |
| 6,322,682 B1 | 11/2001 | Arvidsson et al. |
| 6,379,929 B1 | 4/2002 | Burns et al. |
| 6,454,970 B1 | 9/2002 | Ohman et al. |
| 6,499,499 B2 | 12/2002 | Dantsker et al. |
| 6,591,852 B1 | 7/2003 | McNeely et al. |
| 6,620,478 B1 | 9/2003 | Ohman et al. |
| 6,632,656 B1 | 10/2003 | Thomas |
| 6,653,625 B2 | 11/2003 | Andersson et al. |
| 6,717,136 B2 | 4/2004 | Andersson et al. |
| 6,728,644 B2 | 4/2004 | Bielik et al. |
| 6,811,736 B1 | 11/2004 | Ohman et al. |
| 6,812,456 B2 | 11/2004 | Andersson et al. |
| 6,812,457 B2 | 11/2004 | Andersson et al. |
| 6,852,851 B1 | 2/2005 | Kenrick et al. |
| 6,878,555 B2 | 4/2005 | Andersson et al. |
| 6,884,370 B2 | 4/2005 | Ohman et al. |
| 6,884,395 B2 | 4/2005 | Andersson et al. |
| 6,919,058 B2 | 7/2005 | Andersson et al. |
| 6,955,738 B2 | 10/2005 | Derand et al. |
| 6,967,101 B1 | 11/2005 | Larsson et al. |
| 6,985,672 B2 | 1/2006 | Andersson et al. |
| 6,990,290 B2 | 1/2006 | Andersson et al. |
| 6,992,181 B2 | 1/2006 | Tooke et al. |
| 6,992,278 B2 | 1/2006 | Sjoberg et al. |
| 2002/0025583 A1 | 2/2002 | Ellsworth et al. |
| 2002/0125135 A1 | 9/2002 | Larsson et al. |
| 2002/0150512 A1 | 10/2002 | Kellogg et al. |
| 2003/0029724 A1 | 2/2003 | Derand et al. |
| 2003/0053934 A1 | 3/2003 | Andersson et al. |
| 2003/0054563 A1 | 3/2003 | Ljungstrom et al. |
| 2003/0064004 A1 | 4/2003 | Agren et al. |
| 2003/0066959 A1 | 4/2003 | Andersson et al. |
| 2003/0082075 A1 | 5/2003 | Agren et al. |
| 2003/0129360 A1 | 7/2003 | Derand et al. |
| 2003/0143114 A1 | 7/2003 | Andersson et al. |
| 2003/0156763 A1 | 8/2003 | Soderman |
| 2003/0173650 A1 | 9/2003 | Larsson et al. |
| 2003/0211012 A1 | 11/2003 | Bergstrom et al. |
| 2004/0055136 A1 | 3/2004 | Ohman et al. |
| 2004/0058408 A1 | 3/2004 | Thomas et al. |
| 2004/0096867 A1 | 5/2004 | Andersson et al. |
| 2004/0099310 A1 | 5/2004 | Andersson et al. |
| 2004/0120856 A1 | 6/2004 | Andersson et al. |
| 2004/0202579 A1 | 10/2004 | Larsson et al. |
| 2005/0042770 A1 | 2/2005 | Derand et al. |
| 2005/0129800 A1 | 6/2005 | Ohman et al. |
| 2005/0141344 A1 | 6/2005 | Ekstrand et al. |
| 2005/0153431 A1 | 7/2005 | Andersson et al. |
| 2005/0153432 A1 | 7/2005 | Andersson et al. |
| 2005/0153433 A1 | 7/2005 | Andersson et al. |
| 2005/0153434 A1 | 7/2005 | Andersson et al. |
| 2005/0179901 A1 | 8/2005 | Ostlin et al. |
| 2005/0186685 A1 | 8/2005 | Kange et al. |
| 2005/0202471 A1 | 9/2005 | Tooke et al. |
| 2005/0214442 A1 | 9/2005 | Larsson et al. |
| 2005/0277195 A1 | 12/2005 | Holmquist et al. |
| 2005/0279925 A1 | 12/2005 | Andersson et al. |
| 2006/0002825 A1 | 1/2006 | Derand et al. |

FOREIGN PATENT DOCUMENTS

| | | |
|---|---|---|
| EP | 0282840 A2 | 9/1988 |
| EP | 0745856 A2 | 12/1996 |
| EP | 0977032 A1 | 2/2000 |
| WO | WO-93/22053 | 11/1993 |
| WO | WO-93/22054 | 11/1993 |
| WO | WO-93/22055 | 11/1993 |
| WO | WO-93/22058 | 11/1993 |
| WO | WO-94/26413 | 11/1994 |
| WO | WO-96/06354 A1 | 2/1996 |
| WO | WO-96/07919 | 3/1996 |
| WO | WO-96/14933 | 5/1996 |
| WO | WO-96/15450 | 5/1996 |
| WO | WO-97/07993 | 3/1997 |
| WO | WO-97/21090 | 8/1997 |
| WO | WO-97/45730 | 12/1997 |
| WO | WO-98/07019 | 2/1998 |
| WO | WO-98/15356 | 4/1998 |
| WO | WO-98/22625 | 5/1998 |
| WO | WO-98/38510 | 9/1998 |
| WO | WO-98/39645 | 9/1998 |
| WO | WO-99/58245 | 11/1999 |
| WO | WO-00/25921 | 5/2000 |
| WO | WO-00/40750 | 7/2000 |
| WO | WO-00/62042 | 10/2000 |
| WO | WO-01/02737 | 1/2001 |
| WO | WO-01/30500 | 5/2001 |
| WO | WO-2004/067444 | 8/2004 |
| WO | WO-2004/083108 | 9/2004 |
| WO | WO-2004/083109 | 9/2004 |
| WO | WO-2004/103890 | 12/2004 |
| WO | WO-2004/106926 | 12/2004 |

OTHER PUBLICATIONS

Handique et al., "Microfluidic flow control using selective hydrophobic patterning," SPIE Proceedings, vol. 3224, pp. 185-195, 1997.

MICROFLUIDIC DEVICE

CROSS-REFERENCE TO RELATED APPLICATIONS

This application is a continuation of U.S. application Ser. No. 09/674,457 filed Jan. 2, 2001 which is the National Phase Application of PCT/IB99/00907 filed May 7, 1999 claiming priority to Great Britain Application No. 9809943.5 filed May 8, 1998.

TECHNICAL FIELD

The present invention relates to microfluidic devices which may be used for a variety of biological processes, e.g. screening putative biologically active molecules against cell cultures or separating biological materials, the preparation of such devices and their use.

BACKGROUND OF THE INVENTION

PCT patent application Ser. No. 97/21090 describes a microanalytical/microsynthetic system for biological and chemical analysis which comprises a rotatable microplatform, for example a disk, having inlet ports, microchannels, detection chambers and outlet ports through which may flow.

It has now been found that microfluidic devices can be prepared in which fluid flow may be controlled by having different surfaces of the substrate forming the device having different surface characteristics. By "microfluidic devices" is meant devices that can handle microvolumes of reagents, for example samples of less than 1 µl, suitably less than 500 nl and preferably between 1 and 10 nl, may be introduced into the device. By "fluid" is meant dry powders and liquids, including suspensions of particulates in liquids.

BRIEF SUMMARY OF THE INVENTION

Accordingly, in a first aspect the present invention provides a microfluidic device adapted such that the flow of fluids within the device is controlled by different surfaces of the device having different surface characteristics.

The nature of the surface characteristics which control fluid flow is dependent upon the nature of the fluid itself. For example, when the fluid is a liquid, the surface characteristic that controls the flow of the liquid is preferably the surface energy of the material, e.g. low energy surfaces are normally hydrophobic whilst high energy surfaces are normally hydrophilic. The energy of a surface may be measured in terms of the critical surface tension (see for example Surface and Interfacial Aspects of Biomedical Polymers, Vol 1, Plenum Press, New York, 1985, Ch.7). When the fluid is particulate, the surface characteristic that controls the flow of the particles is dependent upon the nature of the particles, e.g. the surface is treated to interact with the particle, for example if the particle carries a charge the surface will have the same or opposite charge, similarly if the particle is magnetic the surface may be permanently or transiently magnetised.

In one embodiment there is provided a microfluidic device comprising a substrate whose surface is treated to provide areas having different surface characteristics, said areas being arranged to enable control of the flow of fluids passing across the substrate. For example, the substrate may have a hydrophobic surface interspersed with a plurality of hydrophilic areas. Alternatively, the substrate may have a hydrophilic surface interspersed with a plurality of hydrophobic areas. Preferably, the substrate is not formed from a hydrated oxide material. Preferably the substrate is formed from a plastics material such as a polycarbonate or a hydrocarbon polymer (including a halogenated hydrocarbon polymer) such as a polyolefin or a similar material which imparts a hydrophobic surface to the substrate. Whilst the substrate is formed from a material which provides a hydrophobic surface to the substrate, this hydrophobic surface can be treated, as described hereinafter, to convert it to a hydrophilic surface.

Preferably, the device has a second substrate approximately parallel to the first; the first, and optionally the second substrates having surface areas of different surface characteristics that control the flow of fluid within the device.

When the substrate comprises a hydrophobic surface interspersed with hydrophilic areas, these hydrophilic areas suitably comprise a plurality of arrays of hydrophilic spots on the hydrophobic surface. By an array of spots is meant a number of spots, suitably greater than 10 and preferably greater than 50, for example 200, which are arranged on the surface within the same fluid pathway in a predetermined pattern. The array may be single dimensional—i.e. a line of spots, or multi-dimensional.

By areas of different surface characteristics is meant that areas of the surfaces of the substrate have different relative characteristics, for example, in the case of liquids, different relative hydrophobicities or hydrophilicities. Boundaries between such areas may in effect form "walls" defining the flowpath of fluid within the device. Alternatively, they may form "valves" preventing the flow of fluid across the boundary until the fluid has either been provided with sufficient energy to enable it to overcome the difference in surface energies of the surfaces or, if the characteristic of the surface can be imparted to the surface transiently, e.g. in the form of an electric charge, magnetic field, particular temperature or light intensity, by changing the characteristic of the surface.

When a boundary between a hydrophilic and hydrophobic surface is used to create a valve, also referred to herein as a break, the physical parameters associated with the valve, or break, may be designed to give predetermined breakthrough pressures (that is to say the pressure required to make fluid pass over the boundary). Such physical parameters include the dimensions of the valve in terms of its width and breadth compared with the corresponding dimensions of the channel leading into it, the hydrophobicity of the surface forming the valve and, when the device is a rotational disk, the length of the channel leading into the valve.

Normally, it will be possible to pass fluid through a valve of the present invention a number of times. However, certain fluids (for example serum contains a high protein content) may modify the hydrophobic surface making this hydrophilic so that the valve only works once. In this case, when it is desired to add further fluid this will be introduced via a second channel, which also contains a hydrophobic/hydrophilic valve, which connects into the first channel.

It is believed that the terms hydrophobic and hydrophilic are well known to those skilled in the art. That a surface is hydrophobic means that water does not spread on it but stands up in the form of droplets the contact angle being that measured from the plane of the surface, tangent to the water surface at the three phase boundary line. Thus, hydrophobic surfaces have been characterized as having high contact angles with water, often in the range 40 to 110 degrees (Zettlemeyer, Hydrophobic Surfaces, Ed. F. M. Fowkes, Academic Press, (New York). Hydrophilic surfaces are those which have low contact angles with water, often in the range 1 to 25 degrees. However, without limitation and for the purpose of guidance only, suitable hydrophobic surfaces include hydrocarbon polymers, including halogenated hydrocarbon polymers, see for example table 1, whilst suitable hydrophilic surfaces include non-contaminated metal oxides, silicaceous materials, such as glass and polysaccharides. Surfaces of materials may be modified to change their properties, i.e. hydrophilic materials may be given hydrophobic properties by surface treatment with a hydrophobic material such as hydrocarbon, perfluorinated hydrocarbon or silicone containing species. Likewise, hydrophobic materials can be made hydrophilic by the introduction of charged groups or hydroxyl, amide or polyether groups on the surface. It is often convenient to convert the whole (or substantially the whole) of a hydrophobic surface to a hydrophilic surface and to then introduce areas of hydrophobicity onto the hydrophilic surface. A small fraction of a monomolecular layer may be sufficient to change the surface characteristics drastically. When the hydrophobic/hydrophilic boundaries form "walls" and "valves", then the surface energy difference to form a wall may be the same or different to that for a valve, however the energy difference for a wall will normally be higher than that for a valve.

Some or all of the areas interspersed on the surface (be they hydrophobic or hydrophilic) may suitably be treated to allow the culture of cells on them. In this embodiment the device may for example be used for screening intracellular events (see for example European Patent 650396 on how this may be performed).

Suitable liquids for use in the devices of the present invention are those which have a surface tension preferably greater than 18 mNm$^{-1}$ Aqueous solutions or suspensions which have a surface tension greater than 50 mNm$^{-1}$ are preferred.

Suitable particulates for use in the devices of the present invention are powders or beads having a particle size of less than 200 μm. Whilst the present invention anticipates the use of particulates in the devices of the present invention in the absence of a liquid carrier, they may also be present in such a liquid carrier.

The microfluidic device is preferably circular and adapted for rotation about its axis. Such adaptation may take the form of a hole at the axis of one or both substrates which is capable of engaging a drive shaft. Other methods of rotating the device include clamping the device and contacting the perimeter with a moving surface, for example moving wheels, or placing the device on a turntable and spinning the turntable.

When the device is circular the fluid inlet is normally towards the axis of the device. The inlet may be a single port attached to an annular feed channel within the device or it may be a series of ports arranged at spaced angular intervals around the axis. An annular outlet is normally located towards the circumference of the device. Fluid may flow in a laminar manner across the surface of the device or it may flow in channels formed either by hydrophobic/hydrophilic boundaries or by interior walls connecting the two substrates. These interior walls are conveniently arranged radially around the axis of the device. The channels are normally of suitable dimensions to enable capillary forces to act upon the fluid within the channel.

When the device is adapted for cell culture it is preferable to have a source of gases available which aid cell growth. In this case, there will be one or more gas inlets in the device, which are conveniently situated in close proximity to the cells to be cultivated. Gas pathways are provided connecting the gas inlets to the cells or the fluid pathways connected to the cells, enabling culture medium/nutrients and gas, e.g. air, to be supplied down the fluid pathways.

The substrates forming the device are conveniently parallel and are preferably sufficiently close together to enable liquids in the device to be subject to capillary forces, suitably less than two millimeters apart, preferably less than one millimeter. Thus a liquid can be fed into the fluid inlet and will then be sucked down the fluid pathways by capillary action until it reaches a valve conveniently a hydrophobic/hydrophilic boundary, past which it cannot flow until further energy is applied. This energy may for example be provided by the centrifuigal force created by rotating the device. Once the centrifugal force is sufficient, the liquid will flow over the valve and continue in an outward direction until it reaches the annular fluid outlet. When the areas interspersed on the surface are hydrophilic, the fluid will have a surface tension greater than 50 mNm$^{-1}$, for example aqueous solutions or suspensions, and when they are hydrophobic the fluid will be hydrophobic, e.g. non polar organic solvents. Thus, the fluid will be attracted to the areas/spots on the surface.

In one embodiment the areas form arrays of spots of hydrophobicities or hydrophilicities of a predetermined pattern. Such arrays can be used to build up deposits of materials to be analyzed e.g. antibodies, oligonucleotides or a chemical library. For example, droplets of solvents containing the material to be analyzed form on the surface, the solvent evaporates and the material is deposited.

In a second embodiment pathways are formed between parallel substrates. In this case surfaces forming the fluid pathways may themselves have areas of alternating hydrophobicity and hydrophilicity forming arrays of spots as above. These alternating areas of hydrophobicity/hydrophilicity may be formed on the surface of one or both substrates, e.g. one surface may have alternating areas whilst the opposing surface does not.

Alternatively, the fluid pathways may contain a substance for separating chemical/biological materials, e.g. a gel for chromatography or electrophoresis or beads may be trapped in the pathways for carrying out assays; for example, scintillation proximity assays or cells can be trapped in the pathways through specific surface recognition.

Areas of hydrophobicity/hydrophilicity on a surface may be formed by methods well known to those skilled in the art, for example.

1. Masking and Plasma Treatment

This is applicable to most surfaces and enables different degrees of hydrophilicity/hydrophobicity to be achieved with ease. A mask (adhesive tape or cast film) is attached so that it fits tightly to all the surface features. Plasma treatment is then carried out on the non-masked surface.

2. Hydrophilic "photoresist"

The plastic surface is coated with a very thin layer of hydrophilic polymer (e.g. a polyvinylcinnamate) which is crosslinked by illumination through a mask. Non-crosslinked polymer is washed off.

3. Crosslinkable Surface Active Polymer.

A surface active, reactive polymer is adsorbed from aqueous solution to the plastic surfaces and illuminated through a mask. Non-crosslinked polymer is washed off.

4. Polymerizable Surfactants

A monolayer of polymerizable surfactant (e.g. the diacetylene functional phopholipids from Biocompatibles Ltd) is adsorbed and illuminated through a mask. Non-crosslinked surfactant is washed off.

5. Photo-oxidation

The plastic surfaces are illuminated with a powerful light source (e.g. Hg lamp or uv laser) through a mask so that the illuminated areas are oxidized by atmospheric oxygen.

6. Electron Beam Treatment

The plastic is irradiated through a mask so that irradiated areas are in contact with air (or other reactive medium) and are oxidized creating hydrophilic groups.

BRIEF DESCRIPTION OF THE DRAWINGS

In order that the invention may be better understood, several embodiments thereof will now be described by way of example only and with reference to the accompanying drawings in which.

DETAILED DESCRIPTION OF THE INVENTION

Figure 1:
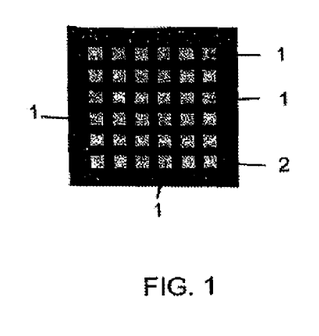
FIG. 1 is a diagram of a surface treated in accordance with the invention.

Referring firstly to FIG. 1, there is shown a mask with an array of 6×6 hydrophilic spots 1, each of 3×3 mm on a 50×50 mm hydrophobic surface 2, which was made in Mac DrawPro and printed on a laser printer. The printout was copied on to a transparency sheet in a copying machine.

The volume of a 25 mm thick film on a 50×50 mm surface 2 is 62.5 ml. This volume polyacrylamid (PAA) was deposited on the hydrophobic side of a Gelbondä film and the above mask was placed on top of thedroplet. The area under the mask was wetted by capillary forces (a small portion of the solution did end up outside the mask). Photopolymerization through the mask was carried out for 3 minutes exposure time. The mask was removed and the surface was rinsed with water. A clear pattern was visible due to the selective wetting at the PAA surface.

Figure 2:
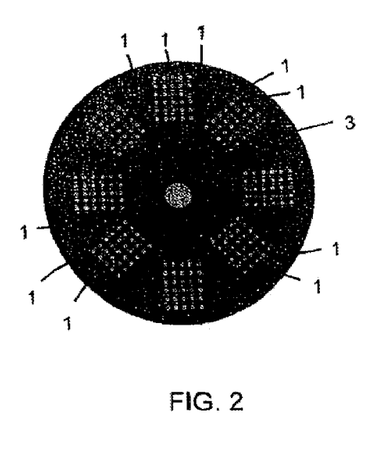
FIGS. 2 and 3 are diagrams similar to FIG. 1, showing different arrangements.
Figure 3:
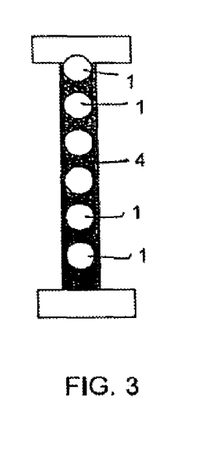

FIG. 2 illustrates a disc substrate 3 having a hydrophobic surface on which are formed eight 6×5 arrays of hydrophilic spots 1. FIG. 3 illustrates a one-dimensional array of hydrophilic spots 1 on a hydrophobic surface 4. As will be explained, with a suitable force applied, a fluid can be caused to pass from spot to spot so that the structure forms a defined channel for fluid flow.

Figure 4:
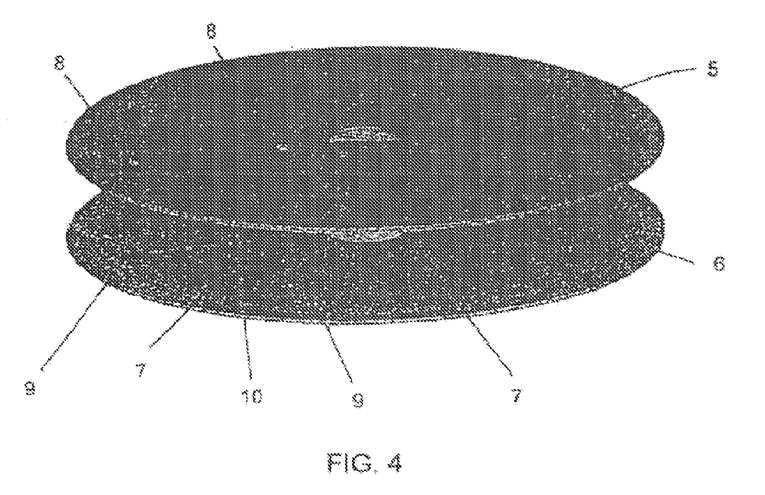
FIG. 4 is a diagram of a twin substrate microfluidic device according to the invention.

FIG. 4 illustrates an arrangement comprising top and bottom plates 5, 6 in the form of rotatable discs, having a common axis of rotation. The discs are illustrated far apart, for the purpose of clarity; in practice, the discs will be spaced apart by a distance defined by annular supporting walls 7 which distance will be suitable for the movement of liquid between the plates by capillary action.

The top disc 5 is provided with inlet holes 8 for supplying liquids to the interior. Lining up with these are corresponding areas 9 on the upper surface of the bottom disc 6, which are hydrophilic. Passing in an axial direction between the areas 9 is an elongate area 10, which is also hydrophilic. The remaining parts of the upper surface of disc 6 are hydrophobic. The elongate area effectively forms a channel for liquid between the areas 9. The hydrophilic surface of area 10, bounded on both sides by the hydrophilic upper surface of disc 6 ensures that the liquid pathway is clearly defined by the "walls" which are formed by the interface between the hydrophobic and hydrophilic areas.

If the discs are rotated together about their common axis, it will be seen that centrifugal force will push liquid along the channel formed by a 10 from the innermost area 9 to the outermost area 9.

Figure 5:
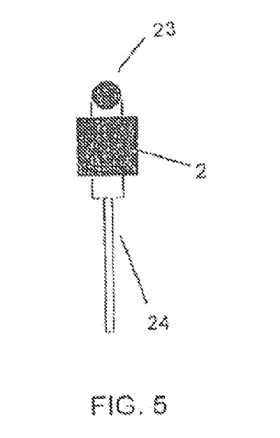
FIG. 5 is a diagram to illustrate the use of hydrophilic areas to grow cells.

FIG. 5 illustrates how cells might be applied to a hydrophilic area 2. An inlet 23 is provided for introduction of cells and reagent and a hydrophobic channel 24 is provided for respiration of the cells during their growth on the area 2 and for rinsing between tests.

Figure 6:
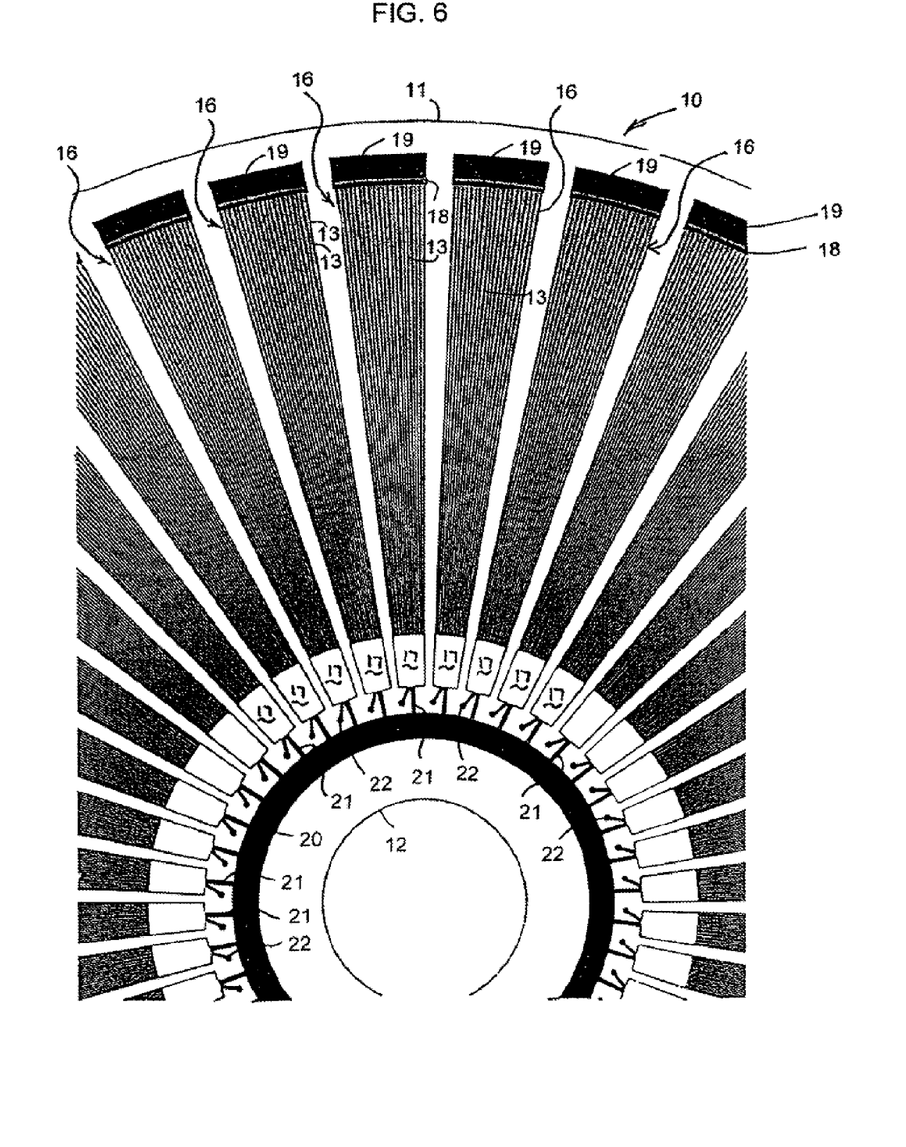
FIG. 6 is a partial plan view of a rotary disc microfluidic device according to the invention.
Figure 7:
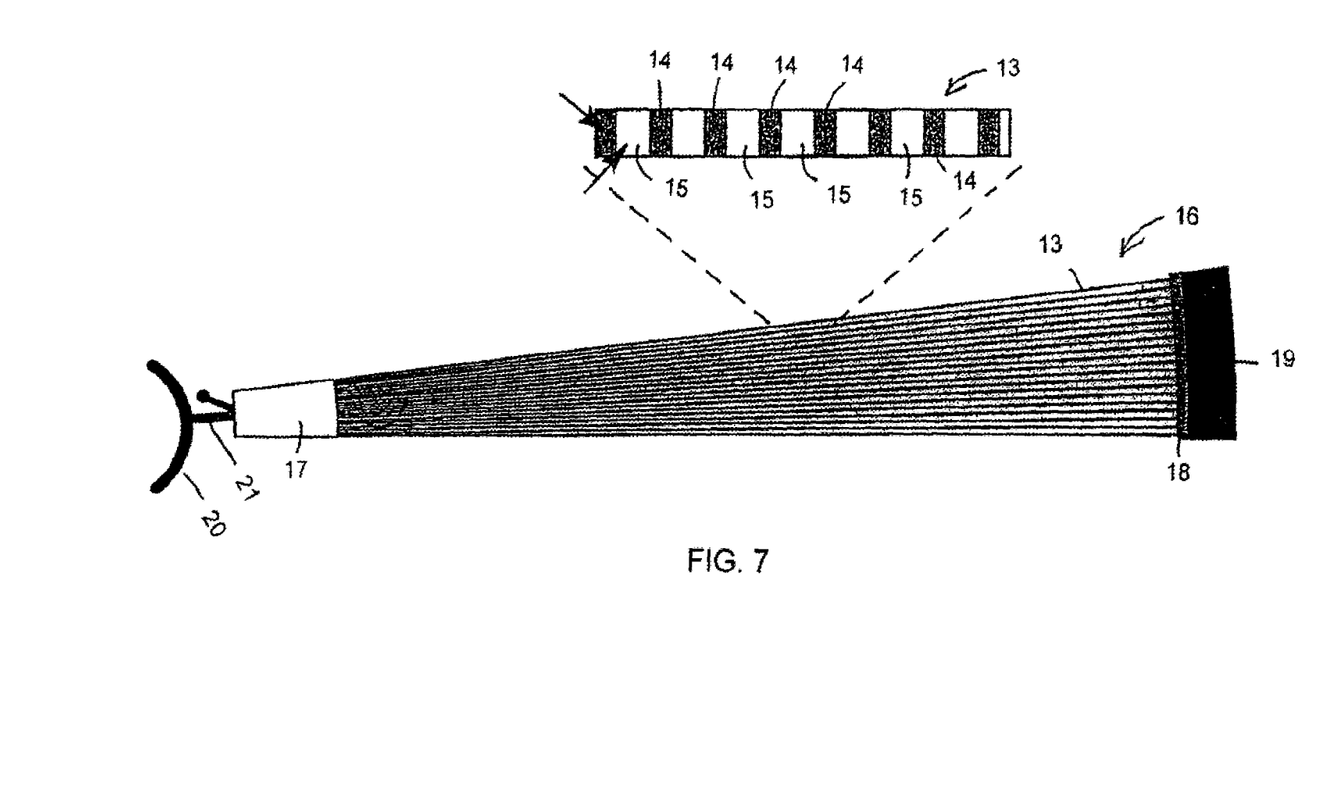
FIG. 7 is a view of part of FIG. 5, illustrated in greater detail.

Reference is now made to FIGS. 6 and 7 which show a microfluidic device in the form of a compact disc (CD) 10 on which are formed hydrophobic and hydrophilic areas to enable liquids to be directed about the surface of the disc to enable the automatic and simultaneous carrying out of multiple chemical/biological tests on multiple samples.

FIG. 6 shows a section of the compact disc 10, having a perimeter edge 11, and central hole 12 about which it may be mounted for rotation within a compact disc reader (not shown). On the surface of the compact disc are formed 40 sector-shaped multi-dimensional arrays 16 of hydrophilic spots. As is made clear in the enlarged view A in FIG. 7, the spots are arranged in individual straight channels 13 radiating radially from the centre of the disc. Each channel comprises alternate hydrophobic areas or breaks 14 and hydrophilic areas or spots 15. The hydrophobic breaks 14 are typically 75 μm wide in the radial direction. The hydrophilic spots 15 are typically 108 μm wide in the radial direction.

In the illustrated embodiment, there are 20 channels in each array 16 and there are 200 hydrophilic spots 15 in each channel. Thus, each array 16 contains 4000 hydrophilic spots.

The channels in each array 16 begin in a common hydrophilic area 17 and end in a common hydrophobic area 18, constituting a break. Positioned radially outwards from the hydrophobic area 18 is a common waste channel 19.

Liquid reagent for use in carrying out the tests is introduced into an inner annular channel 20 which is common to all of the arrays 16. Extending from the channel 20 are 40 radially extending hydrophobic breaks 21, each extending to the hydrophilic area 17 of a respective array 16. A sample to be tested is introduced into the hydrophilic area 16 at 22. In this way, 40 different samples can be tested simultaneously.

Sample testing is carried out by applying to each of the hydrophilic areas 14 a sample of a known reactant, for example a known oligonucleotide. It will be seen that the device has the potential for testing each sample against 4000 different reactants. A cap may be formed on each hydrophilic spot by evaporation and accurate pre-concentration will occur on vaporization.

Next the reagent channel 20 is filled and the disc is spun to cause the reagent to jump across the "valve" caused by the hydrophobic break 21 and radially outwardly to the waste channel 19. Progress along the individual channels 13 is by a series of jumps across the effective "valves" caused by the hydrophilic breaks 14. The force required to overcome the breaks is provided by the centrifugal action of the spinning disc.

Once the reagent is issuing into the waste channel 19 the disc is stopped and liquid sample added at 22. Typically the sample volume is 0.1 μl. The disc is now spun at 2 alternating speeds (for hybridization mixing) whereupon the centrifugal force will move the liquid plug out along channels 13, and capillary action will move the liquid back up. Typically, the sample volume required for each spot 15 is 44 pl.

Reading of the test results is carried out by examining the individual spots 15 using a suitable reader. After the test is completed the disc may be rinsed by the application of a suitable rinse liquid to the channel 20 and spinning of the disc to move the rinse liquid outwardly along channels 13 by centrifugal force.

Figure 8:
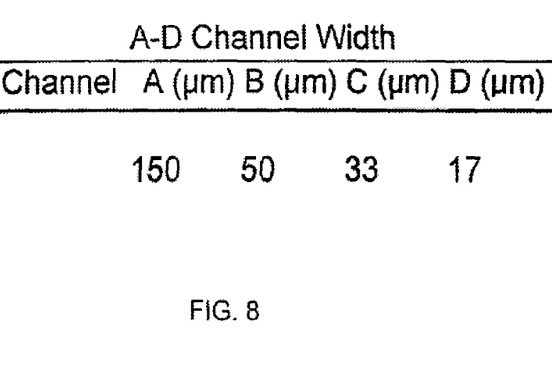
FIG. 8 a section of a microfluidic device in embodiments of the invention having particular channel widths and having two consecutive inner annular hydrophilic channels connected by a radial hydrophilic channel and a channel that contains a hydrophobic area or break.

FIG. 8 shows a section of a CD, 23 having two consecutive inner annular hydrophilic channels, 24 and 25 which are connected by a radial hydrophilic channel 26 and a channel 27 which contains a hydrophobic area or break A. The outermost annular channel 25 is connected to an annular waste channel 28 by a radial hydrophilic overflow channel 29 having a hydrophobic break or valve Y2 adjacent to the junction with the waste channel 28. The annular channel 25 is also connected to two serially arranged chambers 30 and 31, the second of which is in turn connected to the waste channel 28. The annular channels 25 and 28 and the chambers 30 and 31 are connected via channels which contain hydrophobic breaks or valves B, C and D.

The innermost chamber 30 has a treated surface permitting the growth of cells within the chamber. It is also provided with an air channel 32, which contains a hydrophobic break, and which, alternatively, can act as a sample inlet port. The outermost chamber 31 has an untreated hydrophilic surface and can conveniently act as an analysis zone in conjunction with a detector (not shown).

Aqueous reagent for use in carrying out tests is introduced into annular channel 25 and feeds by capillary action into the radial channels until it reaches the hydrophobic breaks or valves B and Y2. The CD is then spun at a first rotation speed so that liquid passes through Y2 into the waste channel 28 and then through B until it reaches C. Cells are allowed to grow in chamber 30 and when cell culture has reached the required level the disc is spun again at a second, higher rotation speed so that the contents of chamber 30 are transferred into chamber 31, but prevented from travelling further by the hydrophobic breaks or valves D. An analysis, or further manipulation, can then be carried out in chamber 31 after which the CD is spun at a third still higher, rotation speed so that the content of chamber 31 passes across D into the waste channel 28.

A rinse solution can then be introduced into the annular channel 24. The CD is spun again so that the solution passes through the hydrophilic breaks or valves Y and A, into the chambers 30 and 31 and then into the waste channel.

In order to prevent capillary "creep" of liquids around hydrophilic corners, a hydrophobic surface was applied to one side of the capillary channels, designated V in FIG. 8. (The channels are normally of square or rectangular cross section. The hydrophobicity and dimensions of the breaks or valves Y, Y2, A, B, C and D are chosen such that the force required to make liquid flow over D is greater than C which in turn is greater than B which is greater than Y2).

The following examples illustrate the preparation of surfaces having different characteristics on a hydrophobic substrate.

EXAMPLE 1

A CD disc made from Zeonex (a cycloolefin copolymer manufactured by Nippon Zeon), having recessed microfabricated channels on the surface, was masked selectively by applying a viscous film-forming fluid at desired spots in the channels. As the film-forming fluid was used either OwocoRod (based on a synthetic water-soluble polymer) or Owoco Rosa (based on a synthetic rubber latex dispersion), both delivered by Owoco AB, Stockholm, Sweden. After drying, the disc was placed in a plasma reactor (Plasma Science PS0500 from BOC Coating Technology, Concord, Calif., USA) and treated with an oxygen plasma (5 cm3/min gas flow, 500 W RFpower) for 10 min. The mask was then removed by water rinsing followed by an ethanol rinse. The non-masked areas had a water contact angle of 5 degrees, while the masked areas had a contact angle of 90 degrees. A soft silicone rubber lid was placed over the disc and an aqueous dye solution was introduced in the channels. The solution penetrated by self-suction into the non-masked channel areas, but stopped at the hydrophobic masked areas. By spinning the disc at 3000 rpm, the solution could be made to pass also over the masked areas.

EXAMPLE 2

A CD disk made from polycarbonate, having recessed microfabricated channels on the surface, was placed in a plasma reactor (Plasma Science PS0500 from BOC Coating Technology, Concord, Calif., USA) and treated with an oxygen plasma (5 cm3/min gas flow, 500 W RF power) for 10 min. After treatment the disc surface had a water contact angle of 5 degrees. A 0.5% solution of polyisobutylene in cyclohexane was then applied locally at selected spots and left to dry in. The polyisobutylene-coated areas had a water contact angle of 100 degrees. A soft silicone rubber lid was then placed over the disc and an aqueous dye solution was introduced in the channels. The solution penetrated by self-suction into the non-coated channel areas, but stopped at the hydrophobic coated areas. By spinning the disc at 3000 rpm, the solution could be made to pass also over the coated areas.

EXAMPLE 3

A C.D. disk made from polycarbonate, having recessed microfabricated channels on the surface, was patterned with gold by evaporation through a shadow mask. First a 40 nm think layer of chromium was evaporated through the mask. The CD disc was then placed in a plasma reactor (Plasma Science PS0500 from BOC Coating Technology, Concord, Calif., USA) and treated with an air plasma (10 cm3/min gas flow, 500 W RF power) for 10 min. After treatment the disc surface had a water contact angle of 6 degrees. The CD disc was then placed in glass container and 50 ml of a 1 mM solution of octadecylmercaptane in ethanol was added.

After one hour in the thiol solution, the CD disc was carefully rinsed by ethanol. The water contact angle on the polycarbonate area was 7 degrees, and 79 degrees on the gold surface. A soft silicone rubber lid was then placed over the disc and an aqueous dye solution was introduced in the channels. The solution penetrated by self-suction into the non-coated channel areas, but stopped at the hydrophobic gold-coated areas. By spinning the disc at 3200 rpm, the solution could be made to pass also over the coated areas.

TABLE 1

| Surface | Water contact angle (degrees) |
|---|---|
| Polytetrafluoro-ethylene (Teflon)* | 108 |
| Polyethylene* | 94 |
| Polypropylene* | 95 |
| Polymethyl methacrylate* | 80 |
| Platinum* | 40 |
| Glass** | "small" |
| Gold* | 65.5 |

*A. C. Zettlemoyer (Hydrophobic surfaces, Ed P M Fowkes, Academic Press (New York) 1969, p. 1-27
**A. W. Adamson Physical chemistry of surfaces 5$^{th}$ ed, Wiley-Interscience 1990, 9 397.

The invention claimed is:
1. A microfluidic device comprising: a circular device which is adapted for rotation about its axis and comprises two substrates, between which there are predetermined hydrophilic channels for liquid flow, and a first hydrophobic section within a hydrophilic channel, wherein at least one channel comprises the first hydrophobic section positioned between two hydrophilic sections in the channel, the hydrophobic section positioned to form a valve that provides a break in liquid flow passing through the channel, wherein the hydrophilic channel has a square or rectangular cross-section and comprises hydrophilic corners, and an additional hydrophobic surface area spaced from the hydrophobic section is applied to only one side of the channel to prevent capillary creep of liquid caused by the hydrophilic corners.

2. The microfluidic device of claim 1, wherein interior walls connecting the two substrates define the channels.

3. The microfluidic device of claim 1, wherein the device comprises an inlet towards the axis of the device.

4. The microfluidic device of claim 1, wherein the device comprises a series of inlet ports arranged at spaced intervals around the axis.

5. The microfluidic device of claim 1, wherein the device comprises an inlet for liquid towards the axis and an annular outlet for liquids towards the circumference of the device.

6. The microfluidic device of claim 1, wherein the channels comprise dimensions enabling capillary forces to act upon the liquid within the channels.

7. The microfluidic device of claim 1, wherein the surface within a channel is treated to enable a culture of cells.

8. The microfluidic device of claim 7, wherein the device further comprises a separate channel containing a hydrophobic section and the separate channel is a gas pathway or a sample inlet.

9. The microfluidic device of claim 8, wherein the separate channel is hydrophobic.

10. The device of claim 1, wherein the liquid comprises a surface tension>18 mNm$^{-1}$.

11. The device of claim 1, wherein the liquid is an aqueous solution or suspension having a surface tension>50 mNm$^{-1}$.

12. A method of producing a microfluidic device having the form of a disc which is adapted for rotation about an axis, and comprising two substrates, at least one of which controls flow of a liquid in the microfluidic device comprising the step of:
treating at least one substrate such that a surface of the treated substrate comprises hydrophilic channels for flow of the liquid and a hydrophobic section or valve within a hydrophilic channel, wherein at least one channel comprises a hydrophobic section positioned between two hydrophilic sections in the channel, the hydrophobic section positioned to prevent flow of the liquid, wherein the hydrophilic channel has a square or rectangular cross-section and comprises hydrophilic corners, and an additional hydrophobic surface area spaced from the hydrophobic section is applied to only one side of the channel to prevent capillary creep of liquid caused by the hydrophilic corners.

13. The method of claim 12, wherein the disc is circular.

14. The method of claim 12, wherein the microfluidic device comprises two parallel substrates for flow of liquids flowing in predetermined channels between the substrates.

15. The method of claim 12, wherein the channels comprise dimensions enabling capillary force to act upon the liquid within the channels.

16. The method of claim 12, wherein treating the surface of at least one of said substrates is selected from the group consisting of masking and plasma treatment, applying a cross-linkable hydrophilic photoresist, adsorbing a crosslinkable surface active polymer, adsorbing a polymerizable surfactant, applying photo-oxidation, applying electron beams, and a combination thereof.

17. A method for controlling flow of a liquid in a microfluidic device comprising the steps of:
providing a microfluidic device which is adapted for rotation about an axis and comprises two substrates, between which there are predetermined hydrophilic channels for liquid flow, and a hydrophobic section within a hydrophilic channel, wherein at least one channel comprises the first hydrophobic section positioned between two hydrophilic sections in the channel, the hydrophobic section positioned to form a valve that provides a break in liquid flow passing through the channel; wherein the hydrophilic channel has a square or rectangular cross-section and comprises hydrophilic corners, and an additional hydrophobic surface area spaced from the hydrophobic section is applied to only one side of the channel to prevent capillary creep of liquid caused by the hydrophilic corners;
adding the liquid to an inlet of the microfluidic device, wherein the liquid flows down the hydrophilic channel until the liquid reaches the hydrophobic section or valve within the channel preventing the flow of liquid; and
applying sufficient energy to the liquid allowing it to pass the valve and continue to flow down the channel.

18. The method of claim 17, wherein the liquid flows down the hydrophilic channel to the valve by capillary action.

19. The method of claim 17, wherein the energy is centrifugal force created by rotating the device about the axis.

20. The method of claim 17, wherein the liquid comprises a surface tension>18 mNm$^{-1}$.

21. The method of claim 17, wherein the liquid is an aqueous solution or suspension having a surface tension>50 mNm$^{-1}$.

22. The method of claim 17, wherein the device is circular.

* * * * *